Figure 1A:
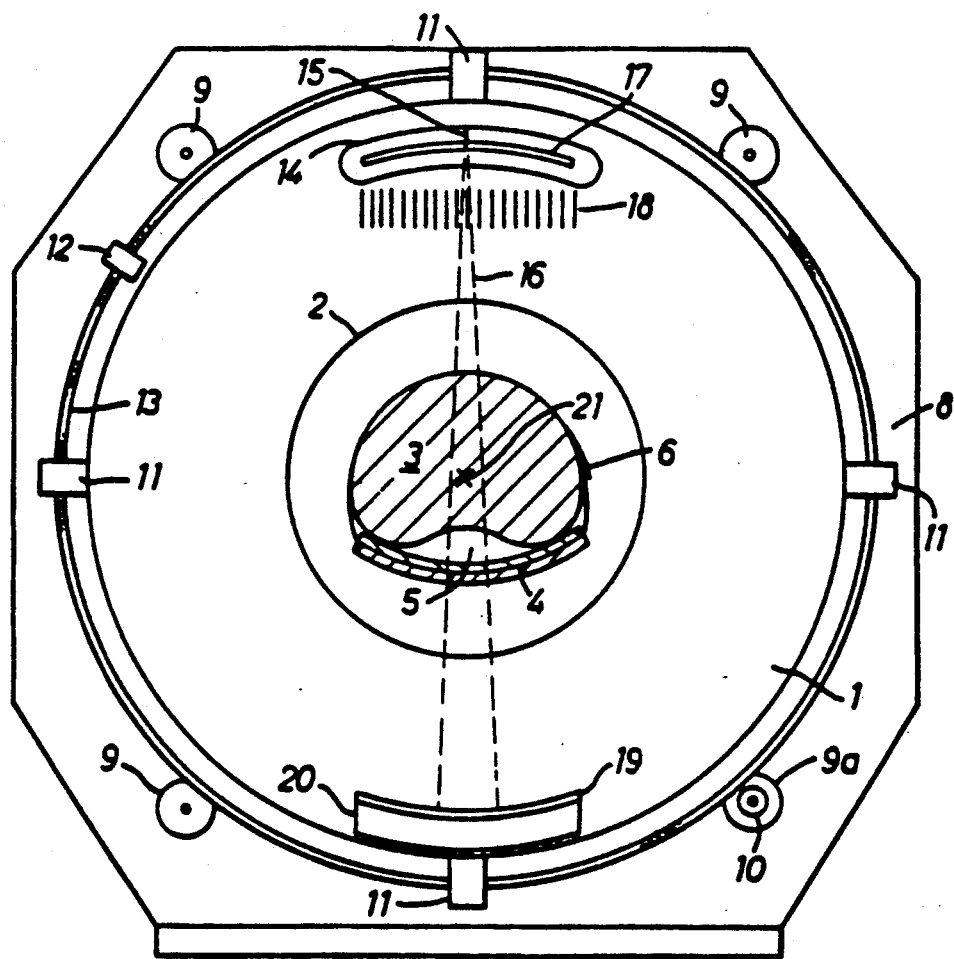

United States Patent [19]

LeMay

[11] Patent Number: 5,218,624
[45] Date of Patent: * Jun. 8, 1993

[54] RADIOGRAPHY

[75] Inventor: Christopher A. G. LeMay, Osterley, England

[73] Assignee: EMI Limited, Hayes, England

[*] Notice: The portion of the term of this patent subsequent to Oct. 18, 2000 has been disclaimed.

[21] Appl. No.: 799,730

[22] Filed: Nov. 22, 1991

Related U.S. Application Data

[63] Continuation of Ser. No. 492,426, Mar. 6, 1990, abandoned, which is a continuation of Ser. No. 240,940, Sep. 6, 1988, abandoned, which is a continuation of Ser. No. 541,892, Oct. 17, 1983, Pat. No. 4,769,828, which is a continuation of Ser. No. 946,644, Sep. 28, 1978, Pat. No. 4,411,011, which is a continuation of Ser. No. 781,345, Mar. 25, 1977, abandoned, which is a continuation of Ser. No. 668,518, Mar. 19, 1976, Pat. No. 4,031,395.

[30] Foreign Application Priority Data

Mar. 20, 1975 [GB] United Kingdom ............... 7366/75
Mar. 20, 1975 [GB] United Kingdom ............... 11553/75
Jun. 21, 1975 [GB] United Kingdom ............... 26485/75

[51] Int. Cl.$^5$ ................................................ A61B 6/02
[52] U.S. Cl. ............................................ 378/10; 378/4
[58] Field of Search .................... 378/4, 10, 11, 12, 13, 378/14, 15, 19, 901

[56] References Cited

U.S. PATENT DOCUMENTS

| | | | |
|---|---|---|---|
| 4,002,917 | 1/1977 | Mayo | 378/14 |
| 4,057,725 | 11/1977 | Wagner | 378/9 |
| 4,411,011 | 10/1983 | LeMay . | |
| 4,769,828 | 9/1988 | LeMay | 378/4 |
| 4,833,698 | 5/1989 | Flannery et al. | 378/901 |

Primary Examiner—David P. Porta
Attorney, Agent, or Firm—Cooper & Dunham

[57] ABSTRACT

In a radiographic apparatus, a source of radiation is arranged to scan a planar spread of radiation in a plane about the body of a patient being examined. A plurality of detector devices is arranged to provide data representing the absorption of the radiation along a plurality of paths within the spread, for different orientations in the plane, for processing to determine a distribution of absorption coefficients for a planar slice of the body. The arrangement is such that a predetermined number of the detector devices are irradiated by the spread of radiation at any time and the actual devices irradiated change progressively as the scan progresses.

10 Claims, 4 Drawing Sheets

RADIOGRAPHY

This is a continuation of application Ser. No. 492,426, filed Mar. 6, 1990, now abandoned which in turn is a continuation of application Ser. No. 240,940 filed Sep. 6, 1988 (now abandoned), which in turn is a continuation of application Ser. No. 541,892 filed Oct. 17, 1983 (now U.S. Pat. No. 4,769,828), which in turn is a continuation of application Ser. No. 946,644 filed Sep. 28, 1978 (now U.S. Pat. No. 4,411,011), which in turn is a continuation of application Ser. No. 781,345 filed Mar. 25, 1977 (now abandoned), which in turn is a continuation of application Ser. No. 668,518 filed Mar. 19, 1976 (now U.S. Pat. No. 4,031,395).

The present invention relates to radiographic apparatus of the kind arranged to provide a representation of the variation of absorption with position across a planar slice of a body with respect to penetrating radiation.

In U.S. Pat. No. 3,946,234 there is described an apparatus for that purpose which includes a source of penetrating radiation arranged to provide a fan-shaped spread of radiation lying in the plane of the slice. Suitable collimators are provided to define a plurality of pencil beams from that spread and an array of detectors is arranged to measure the intensity of each of those beams after passage through the body. The detectors are required to provide output signals indicative of the absorption suffered by the radiation over a large number of paths through the body. For that purpose the source and detectors are reciprocated in the plane of the slice and orbited about a common axis normal to that plane. The output signals are processed by any suitable method, for example the convolution method described in U.S. Pat. No. 3,924,129, to provide the desired representation.

Further developments of the apparatus is described in U.S. Pat. No. 3,937,963 and U.S. application Ser. No. 544,799. According to those specifications the fan-shaped spread of radiation subtends an angle sufficient to include the whole region of interest in the plane of the slice so that a complete scan can be effected solely by orbiting the source and detectors about the common axis.

It is an object of the present invention to provide an alternative apparatus for the same purpose.

According to the invention there is provided an apparatus for examining a body by means of penetrating radiation including a source means arranged to irradiate the body with a planar spread of said radiation, detector means arranged to detect the radiation to provide output signals, relating to absorption of the radiation by the body, for processing to provide a representation of the distribution of absorption in a substantially planar section of the body and means adapted to scan the planar spread of radiation in relation to the body so as to irradiate said section along a plurality of beam paths passing through the body from a plurality of directions, wherein said detector means comprises a plurality of detector devices of which a predetermined number are irradiated by said spread at any time and wherein the scanning means is arranged to traverse the spread of X-rays along the detector devices so as to change the irradiated devices progressively.

According to a feature of the invention the detector devices are interconnected in groups of which not all devices are irradiated at any time so that the outputs of all devices in any group are provided as one output channel for the said processing.

Figure 2:
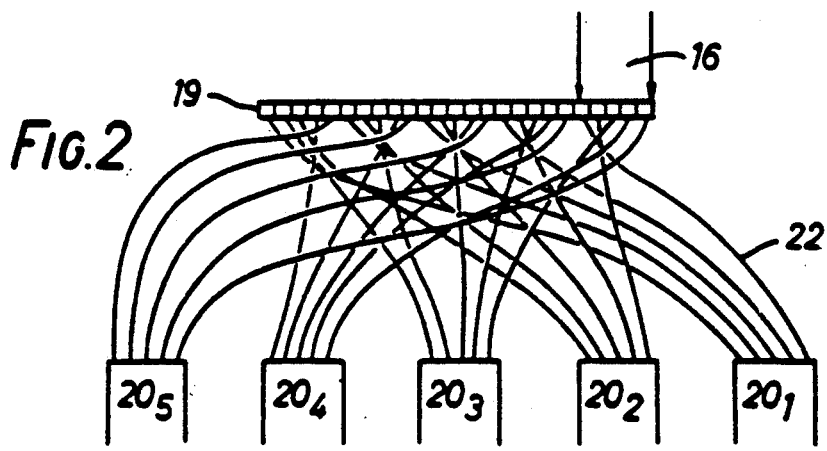
Figure 1B:
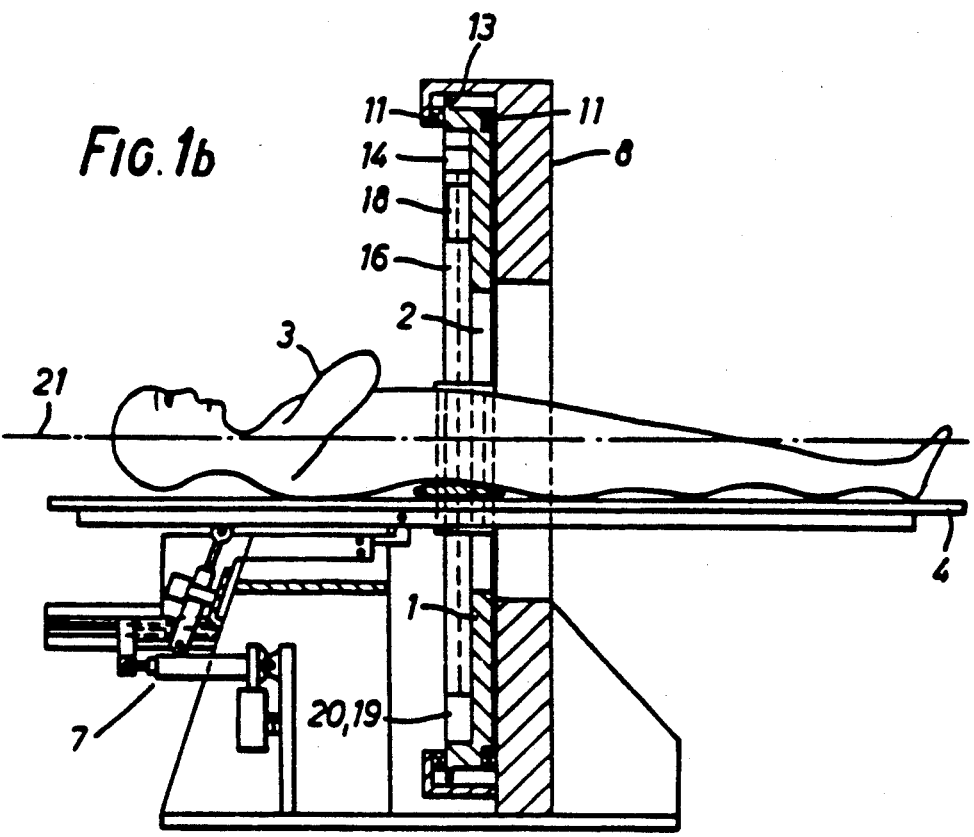
Figure 3:
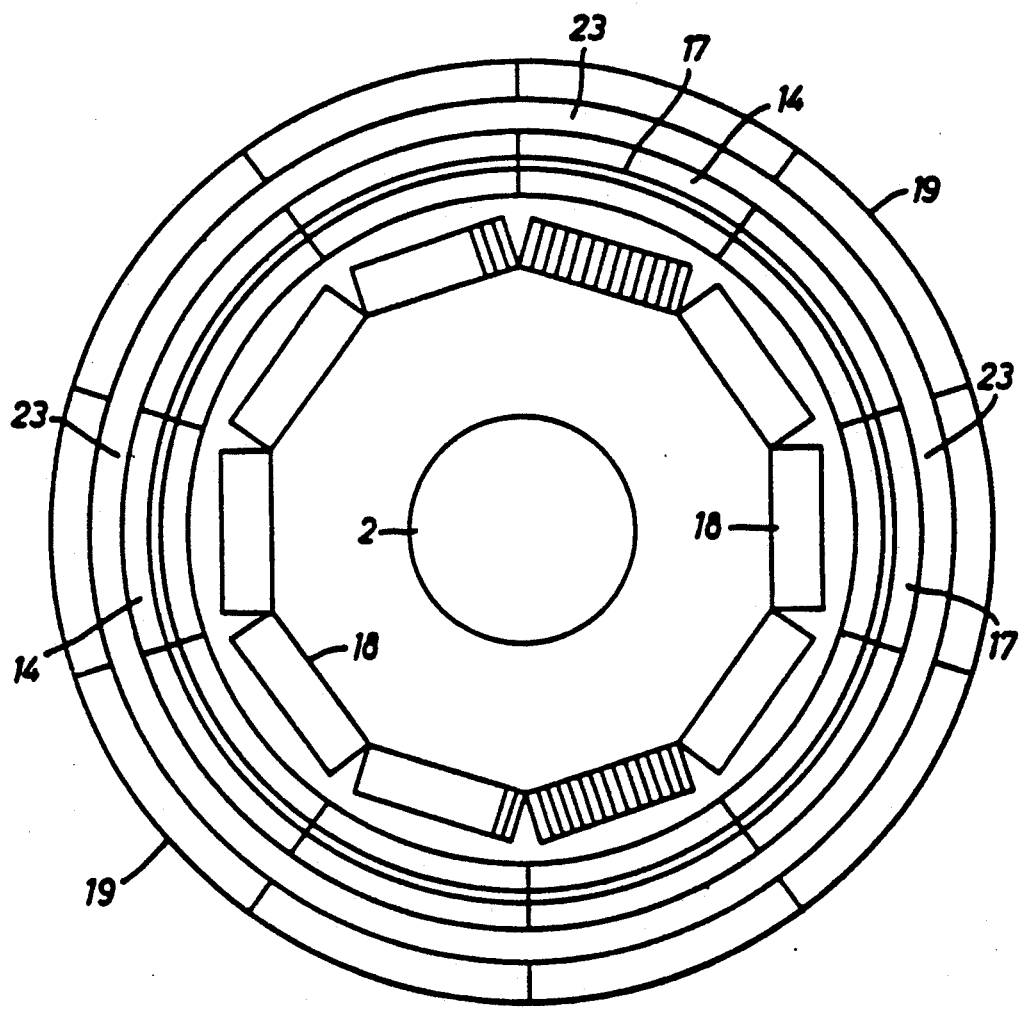
Figure 4:
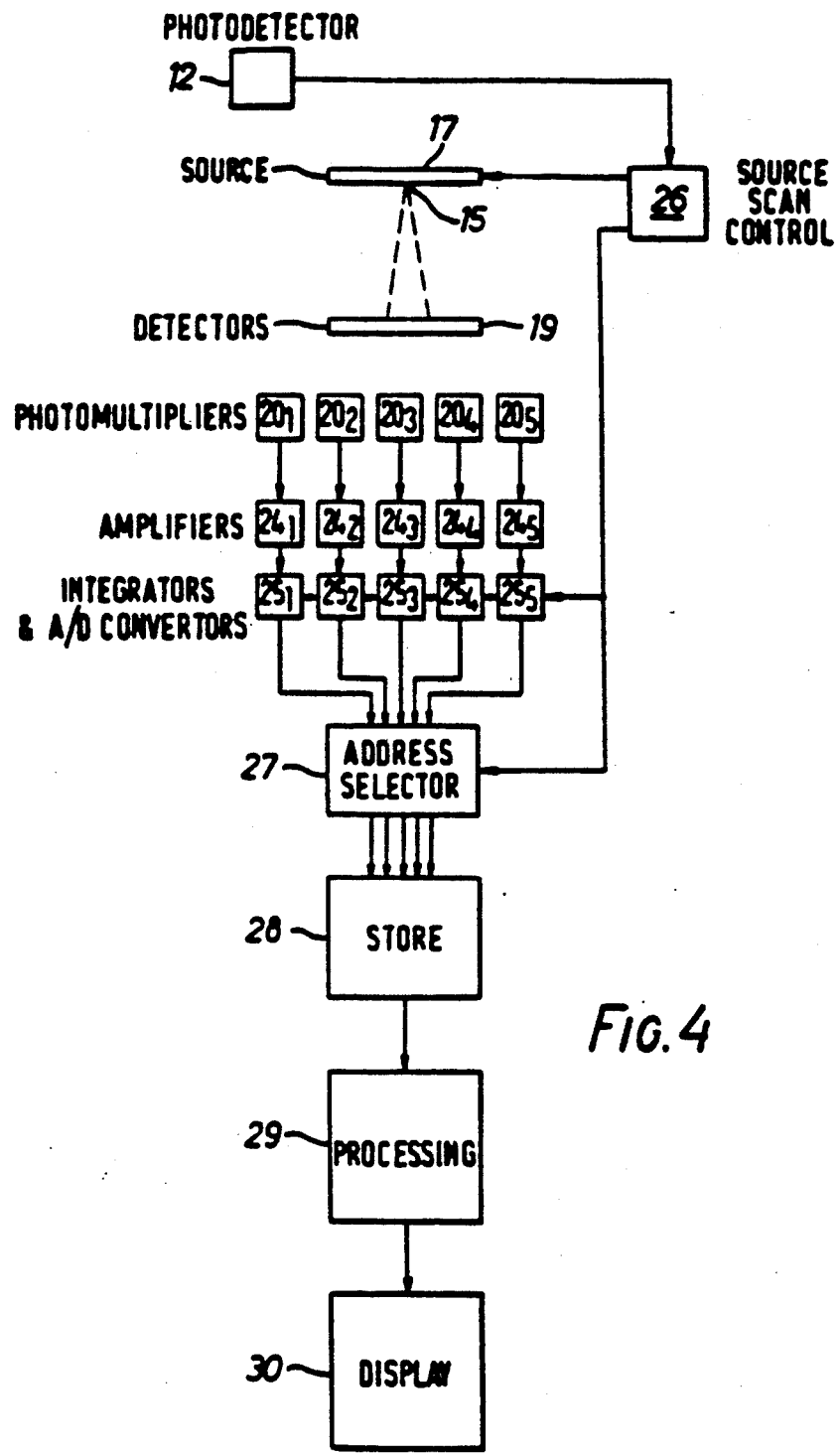

In order that the invention may be clearly understood and readily carried into effect, examples thereof will now be described with reference to the accompanying drawings of which, FIGS. 1a and 1b show in simplified form, in end and slide elevation respectively, an apparatus incorporating the invention, FIG. 2 shows a detector arrangement for one example of the invention, FIG. 3 shows an arrangement for an alternative embodiment of the invention and, FIG. 4 shows in block diagrammatic form a circuit used for processing data derived from the apparatus.

The apparatus is shown in a simplified form in end elevation in FIG. 1a and in side elevation in FIG. 1b and comprises a rotary member 1, which is rotatable about an aperture 2 in which the body 3 of a patient to be examined can be inserted. The body 3 shown in transverse section is supported on a suitably shaped bed 4 also shown in transverse section. A material 5 having an absorption to the radiation similar to body tissue is positioned between the body 3 and the bed 4 to substantially exclude air from the gap therebetween the is extended partly about the body to provide an approximately circular cross section to the radiation. The body is retained firmly in the desired position by means such as a restraining strap 6. If desired a more rigid arrangement such as that shown in U.S. Pat. No. 3,946,234 can be used.

Means for properly positioning bed 4 may take any suitable form and are indicated generally at 7. The rotary member 1 is rotatably mounted on a fixed frame 8, having an aperture at least commensurate with aperture 2. Member 1 is rotated by means of a gear wheel 9a journalled in frame 8 and driven by a motor 10. The gear wheel 9a engages gear teeth, not shown, formed around the periphery of member 1. Other, non driven, gear wheels 9, also journalled in frame 1a, are also provided to properly support rotary member 1 and bearings 11 are provided to restrict axial motion. A light source/photocell device 12 fixed to main frame 18 cooperates with a graticule 13 to provide pulses indicative of the progress of the rotary motion. Graticule 13 is formed around the entire circumference of member 1 and comprises a transparent substrate having opaque markings formed thereon. By interrupting the light path between light source and photocell these markings provide the desired pulses. Other means of providing suitable pulses may of course be used.

The rotatable member 1 carries a source 14 of penetrating radiation. This may be similar to the source described in U.S. Pat. No. 4,002,917 in which a substantially point source 15 of X-rays 16 is scanned over an elongated anode 17 by the scanning of an incident electron beam be means not shown. The X-rays 16, which are confined to a fan-shaped spread by suitable collimator means 18, are, after passage through the body, incident on a detector means 19. Detector means 19 will be described in greater detail hereinafter.

Also carried on member 1 is the collimator arrangement 18. This comprises in this example a plurality of thin parallel plate collimators, made of molybdenum or other suitable material, which are arranged to define the X-rays 16 into a narrow fan of X-rays directed at detector 19 and having the same angular spread for all positions of the spot 15. Other collimators, not shown, restrict the X-rays to the plane of the slice to be examined. The collimators are shown in simplified form in FIG. 1 and in one practical example are plates two thousands of an inch (mils) thick, 900 mils long and at 18 mils spacing. Considering a typical dimension of X-rays spot 15 on the anode 17 of the tube 14 to be 80 mils diameter it will be apparent that the fan of X-rays is formed by four or five collimator slits so that the motion of the X-ray fan, on detector 19, in response to movement of spot 15 is substantially steady. It should be noted that the intensity distribution across the fan, produced by the collimator arrangement, should be taken into account in processing. A collimator arrangement of the dimensions given can be used to give a fan of about 2° extent if placed at a suitable distance from the source. In this example of the invention a fan of substantially 1.8° is considered.

The detector means 19 comprises a strip of individual detectors such as scintillator crystals or photodiodes, lying in the plane of the slice to be examined so as to intercept substantially all of the X-rays 16 for all positions of the spot 15. As shown in FIG. 1a this strip of detectors is only irradiated over a small portion at any time. For the purposes of explanation it will be assumed that 3 cm of the strip is so irradiated at any time. The detector comprises detector elements each covering 1 mm of the strip so that thirty such elements supply data across the 3 cm of the fan. This data corresponds to thirty individual beam paths in the fan. The entire detector is typically 30 cm long including 300 detector elements. In this example the detectors are scintillator crystals co-operating with photomultipliers indicated generally at 20.

In operation the X-ray spot is scanned steadily across the anode 17 of tube 14 and correspondingly the fan of X-rays 16 scans in a plane across body 3 and surrounding materials and along detector strip 19. In this example the irradiated region of the detectors moves in the same direction as and approximately parallel to the source spot 15 as a result of the form of collimators 18 used. The outputs of the detector elements are integrated for a period in which the irradiated region of the detectors is moved 1 mm so that each detector provides one datum for a respective beam path. For the immediately following integration interval the data are obtained for elements displaced one place in the direction of scan i.e. with an extra element at one end of the irradiated region and one less at the other. The detector elements irradiated are thus progressively changed as the scan progresses.

It can be seen that by this means the information relating to any one small region of the body is obtained by many detectors so that the effect of relative detector errors is reduced.

To irradiate the body over a sufficient number of beam paths source 14 and detector means 19 are in this example orbited about an axis 21 perpendicular to the slice of the body 3 to be examined. This may be achieved in steps between each scan of the spot 15. However, since the angle of the fan is 1.8° this will be the required orbital movement for one lateral scan and it is sufficiently small to be provided by a continuous orbital movement without significant distortion or misplacement of the beam paths.

As mentioned hereinbefore, at any time only a small proportion of the detector elements of detector means 19 are irradiated, typically thirty out of three hundred.. That situation is utilised in the detector arrangement shown in FIG. 2. The figure shows, for the sake of clarity, a simplified arrangement for which detector means 19 comprises twenty five detector elements, in the form of scintillation crystals, of which only five are irradiated at any time. The intensity of light emitted by the scintillators is measured by five photomultipliers $20_1$ to $20_5$ each of which receives light from five detector elements through individual light guides 22. The light guides are represented in the Figure by single lines. However it will be understood that each light guide in practice receives light from one entire face of a crystal, the other faces being silvered to prevent loss of light. The light guides 22 are arranged so that the photomultipliers receive light from detector elements in interlaced manner. In this example each receives light from elements spaced five positions apart. It will be seen from FIG. 2 that, although each photomultiplier receives light from five detector elements, only one of these will be irradiated at any time. Thus, for the position of X-ray fan 10 shown in FIG. 2, each photomultiplier receives light along the first light guide from the right, at the multiplier, and no light along the others. As the fan moves one element to the left only the light to photomultiplier $20_5$ changes so that light is received along the second light guide. It will be apparent that, in this manner, the twenty five detector elements can be covered by the five multipliers if the data from these multipliers is appropriately allocated in the processing used. Other numbers of detector elements and photomultipliers may be used in a similar manner.

Instead of using five different photomultipliers a five, or more channel photomultiplier can be used. This may be of the type described in U.S. Pat. No. 3,872,337. This may equally well be a three hundred channel photomultiplier if desired. In that case the photomultiplier can be placed close to the detector elements with short, or no light guides so that each element would at all times supply light to one photomultiplier channel. However, since, as described above, only a small number of detector elements are irradiated at any time a grouping similar to that of FIG. 2 can be effective by joining the photomultiplier channel anodes in groups internally. By this means the number of output connections required would be reduced, simplifying construction problems. As in the previous example other numbers of irradiated elements and groupings may be employed as desired.

It should be understood that FIG. 2 is illustrative of a manner of organising the detector output. However other positions, for example of photomultipliers 20, can be adapted for convenience of construction.

As mentioned hereinbefore large numbers of detector elements are employed in a practical arrangement, typically 300 arranged in six cycles of fifty elements. Fifty detector elements, say 1 mm apart, can be irradiated by the narrow fan of X-rays, the individual fifty beam paths being narrow enough to give the desired spatial resolution within the body. This results, however, in a large quantity of output data and, since the angular resolution so obtained is unnecessarily good, some of this data may be combined to give reduced angular resolution. The arrangement in this example is that data for beam paths passing through substantially the same parts of the body should be combined. In practice, this means that data for each beam in the fan is combined with data obtained from beams incident on a number of, say three, adjacent detectors and passing through the same predetermined point in the body. A time delay of $\tau$ of seconds is applied between those adjacent detectors. The delay $\tau$ is equal to the time which elapses between the passage of a beam incident on one detector through the predetermined point and the passage of a beam incident on the next detector through the same point. The data for the first detector is delayed $\tau$ seconds and added to that of the second and the two are delayed by a further $\tau$ seconds and added to the data for the third detector. The arrangement is assumed to be that employing continuous orbital motion thus the three beam paths for which data is combined are not strictly parallel but give a composite beam path which is narrower at the centre of the body and slightly thicker at the edges. For three beam paths this does not give significant error but allows a reduction of storage to one third of that otherwise required.

In an alternative mode of operation of apparatus such as that of FIG. 1 the X-ray spot scan and collimators 18 can be arranged so that the fan effectively rotates about the body, with the region of irradiated detectors moving laterally in the opposite direction to the source spot. If the extent of anode 17 and detectors 19 is sufficient the orbital motion may be dispensed with. In that case the organisation of the data can be similar to that described in U.S. Pat. No. 4,206,359. As a further alternative the scanning X-ray source can be replaced by a conventional source such as a rotating anode tube and the scan of the fan of X-rays relative to the detectors provided solely by orbital and/or lateral scanning motions of that source.

It should be noted that, in the arrangements described, afterglow in detector elements no longer being irradiated can still be intercepted by the photomultipliers and introduce some noise into the data. For this reason scintillator crystals having low afterglow should be employed. The problem can be alleviated by the use of other detectors such as semiconductor diodes, which may be germanium photodiodes. Gas filled counters or other detectors may also be used. In those cases the group, if desired, may be by suitable multiplexing of the output signals. Alternatively shutter means or similar may be provided to intercept the emitted light between the crystals and the associated photomultipliers.

FIG. 3 shows a development, of the arrangement described, for which the orbital movement, of X-ray source 14 and detector means 19, is not required. Aperture 2 is surrounded by a ring of individual scanning X-ray tubes 14 of which the glass envelopes, indicated at 23 are arranged to adjoin. Inside the ring of tubes 14 there is provided a ring of collimators 18. X-ray tubes 14 having anodes 17 and collimators 18 are essentially similar to those described in relation to FIG. 1, tubes 14 being fixed in relation to the body in aperture 2. Outside of tubes 14 there is provided a further ring comprising a plurality of detector means 19 each of which is as described hereinbefore.

At any time one of the tubes 14 is in operation, the X-rays being formed into a fan by collimators 18 nearest to the tube and thereafter passing through the body in aperture 2 to be received at a detector means 19 opposite. It will be understood that for this purpose the ring of detector means 19 must be set in a sufficiently different plane from tubes 14 for the X-rays to reach the detectors unobstructed. This is a source of slight error in the desired data but such errors largely cancel for the data obtained from the 180° displaced detector. Collimators 18 may be arranged so that the beam passes through them after passing through the aperture 2 as well as before.

In operation the X-ray tubes are operated in sequence so that the X-ray spot on the anode orbits in effect around the body in aperture 2. The ring of collimators 18 is arranged to rotate around aperture 2 but at a relatively slower rate than the rotation of the FIG. 1 arrangement. The angular velocity desired is such that the collimators move through an angle slightly less than the beam spread angle, of the fan of X-rays 16, during one revolution of the X-ray spot. In the example shown in FIG. 3 the collimator is in ten sections so that, without rotation, the angle of the centre beam of the fan would change by 36° when the spot moves from one section to the next. For the 1.8° fan of the example the collimators rotate 1.8° in one spot revolution so that, when the spot returns to the same collimator section it begins to fill in the missing 36°. Thus twenty revolutions of the spot are required to fill in all missing values. The exact number used is tailored to give a suitable degree of overlap between fan beams for adjacent positions to reduce noise problems. It will be apparent that this collimator movement changes the fan position by 0.18° as it crosses each section but such a small error can be disregarded. It should be noted that any detectors not being irradiated may be switched out of the circuit by any suitable means to reduce noise problems further.

In an alternative mode of operation of the FIG. 3 arrangement, the fan of radiation may be of sufficient extent to encompass the entire region of interest in the body. In that case, in conjunction with larger source and detector sectors, the operation would be such that the position of the group of detectors irradiated by the fan orbits in effect about the body in the same direction as the source spot.

FIG. 4 shows in simplified block diagrammatic form an arrangement for processing the output signals derived by the arrangement of FIG. 2 disregarding the steps required for combining adjacent detector outputs with appropriate delays. The five photomultipliers $20_1$ to $20_5$ are shown although it will be understood that there may be a greater number of photomultipliers or outputs from a single photomultiplier. The signals are amplified in amplifiers $24_1$ to $24_5$ and integrated and converted to digital form in converters $25_1$ to $25_5$. The integration period is as allowed by the progress of the scan of the X-ray source spot 15 and is controlled by signals from a scan control unit 26, which also controls the source spot 15. Scan control unit 26 also receives signals from photodetector unit 12, related to the progress of the orbital scan, so that the scan of source spot 15 can be properly related to the orbital movement. The data are provided to appropriate locations in a store 28 in response to an address selector 27. The locations in store 28 are chosen so that successive outputs from each photomultiplier are applied to storage locations representing beam paths at successive angles in the fan. After the fifth such angle, in this example, the data are applied to a new location representing a parallel beam path again at the first angle and the cycle recommenced. In this way the data are allocated to storage locations representing five sets of data each for parallel beam paths at one of the angles of beams in the fan, the allocation taking into account the grouping of outputs shown in FIG. 2. When store 28 contains data for the complete sets of beam paths, properly sorted this data is applied to a processing unit 29 for processing, for example, as described in U.S. Pat. No. 3,884,129 or in U.S. Pat. No. 3,778,614. The processing derives absorption values for individual elements of a matrix of elements notionally delineated in the planar slice being examined. The values are then provided as signals applied to corresponding elements of a representation on a display unit 30. Unit 30 may be a cathode ray tube, line printer or other suitable output device. Alternatively it may be applied to permanent storage, not shown, for future display.

The apparatus described hereinbefore is intended to acquire all the required data in a very short time, possibly as short as one hundredth of a second for the arrangement of FIG. 3. A suitable analogue to digital converter should be employed to meet such rates of acquisition. Such a converter may operate in the known manner of converting the output of a digital counter to analogue form and counting up or down to match that output to the input voltage. However it may be divided into a plurality of sections each to convert to digital form signals between preset threshold levels, to operate at a faster rate.

It will be appreciated that the invention is not limited to the forms described hereinbefore and that other arrangements may be devised.

What I claim is:

1. A system for examining an object comprising:
   a detector of penetrating radiation surrounding a transverse slice of the object at least halfway; and
   a source which irradiates, with penetrating radiation coming from an origin which moves relative to said detector along at least one curved path extending at least halfway around the slice, both said slice and at least a portion of said detector which at the time is across the slice from the origin;
   wherein successive positions of the origin along said at least one curved path are not spaced from each other by detectors; and
   wherein the source comprises at least one anode which substantially conforms to said curved path and is scanned with an electron beam to produce an origin of the penetrating radiation which moves along the anode in a plane conforming to said slice.

2. A system as in claim 1, in which said at least one anode is in the form of an arc whose angular extent is substantially less than 360°.

3. A system as in claim 1 in which said detector comprises a curved array of detector elements extending along an arc conforming to the a plane defined by said slice.

4. A system as in claim 1 in which said detector and said curved path of said origin of the radiation are spaced from each other along a direction transverse to said slice.

5. A system as in claim 1 including circuits for deriving signals from said detector related at least to penetrating radiation received at said detector and circuits utilizing said signals to generate an image of said slice.

6. A system as in claim 5 in which said circuits generating an image of said slice comprise circuits carrying out filtered backprojection.

7. A method comprising:
   irradiating a body with penetrating radiation coming from at least one anode which is scanned with a beam of radiation which is different from said penetrating radiation in a plane conforming to a slice of said body;
   detecting penetrating radiation which has passed through the body to generate detector outputs related to the detected radiation; and
   using said detector outputs to image said slice.

8. A method as in claim 7 in which said using step comprises computerized reconstruction of said image.

9. A method as in claim 8 in which said computerized reconstruction comprises filtered backprojection.

10. A method as in claim 7 in which said body is a patient.

* * * * *